United States Patent
Holenz et al.

(10) Patent No.: US 7,550,624 B2
(45) Date of Patent: Jun. 23, 2009

(54) PHARMACEUTICALLY ACTIVE SALTS AND ESTERS OF 1-DIMETHYLAMINO-3-(3-METHOXY PHENYL)-2-METHYLPENTAN-3-OL AND 3-(3-DIMETHYLAMINO-1-ETHYL-1-HYDROXY-2-METHYLPROPYL)-PHENOL AND METHODS OF USING SAME

(75) Inventors: Joerg Holenz, Barcelona (ES); Helmut Buschmann, Esplugues de Llobregat (ES)

(73) Assignee: Gruenenthal GmbH, Aachen (DE)

( * ) Notice: Subject to any disclaimer, the term of this patent is extended or adjusted under 35 U.S.C. 154(b) by 775 days.

(21) Appl. No.: 11/003,534

(22) Filed: Dec. 6, 2004

(65) Prior Publication Data
US 2005/0143355 A1 Jun. 30, 2005

Related U.S. Application Data

(63) Continuation of application No. PCT/EP03/05971, filed on Jun. 6, 2003.

(30) Foreign Application Priority Data
Jun. 6, 2002 (DE) .............................. 102 25 315

(51) Int. Cl.
C07C 69/00 (2006.01)
C07C 13/36 (2006.01)
C07D 209/18 (2006.01)
A61K 31/60 (2006.01)
A61K 31/40 (2006.01)
A61K 31/205 (2006.01)

(52) U.S. Cl. ........................ 560/143; 562/490; 548/495; 514/165; 514/420; 514/554

(58) Field of Classification Search ................. 560/143; 562/490; 548/495; 514/165, 420, 554
See application file for complete search history.

(56) References Cited

U.S. PATENT DOCUMENTS 6,344,558 B1 * 2/2002 Buschmann et al. .......... 544/86

OTHER PUBLICATIONS

Ibuprofen From Wikipedia.*

* cited by examiner

*Primary Examiner*—Sikarl A Witherspoon
(74) *Attorney, Agent, or Firm*—Crowell & Moring LLP

(57) ABSTRACT

Pharmaceutically active salts and esters of 1-dimethylamino-3-(3-methoxyphenyl)-2-methylpentan-3-ol and 3-(3-dimethylamino-1-ethyl-1-hydroxy-2-methylpropyl)-phenol, and methods of using the same for treating or inhibiting increased urinary urgency or urinary incontinence and/or pain.

12 Claims, No Drawings

PHARMACEUTICALLY ACTIVE SALTS AND ESTERS OF 1-DIMETHYLAMINO-3-(3-METHOXYPHENYL)-2-METHYLPENTAN-3-OL AND 3-(3-DIMETHYLAMINO-1-ETHYL-1-HYDROXY-2-METHYLPROPYL)-PHENOL AND METHODS OF USING SAME

CROSS REFERENCE TO RELATED APPLICATIONS

This application is a continuation of international patent application no. PCT/EP03/05971, filed Jun. 6, 2003 designating the United States of America, and published in German as WO 03/103650 on Dec. 18, 2003, the entire disclosure of which is incorporated herein by reference. Priority is claimed based on Federal Republic of Germany patent application no. DE 102 25 315.3, filed Jun. 6, 2002.

BACKGROUND OF THE INVENTION

The present invention relates to active constituent salts and esters of 1-dimethylamino-3-(3-methoxyphenyl)-2-methylpentan-3-ol and 3-(3-dimethylamino-1-ethyl-1-hydroxy-2-methylpropyl)-phenol, processes for their production, their use for the production of a medicament for the treatment of increased urinary urgency and urinary incontinence, as well as corresponding medicaments and processes for the treatment of increased urinary urgency, urinary incontinence and pain.

Urinary incontinence is the involuntary voiding of urine. This occurs in an uncontrolled manner if the pressure within the bladder exceeds the pressure that is necessary to close the ureter. Causes may include on the one hand an increased internal bladder pressure (for example due to detrusor instability) resulting in urgency incontinence, and on the other hand a reduced sphincter pressure (for example after childbirth or surgical intervention), resulting in stress incontinence. The detrusor is the collective term for the coarse bundles of multilayer muscles of the bladder wall, whose contraction leads to release of urine; the sphincter is the constrictor muscle of the urethra. Mixed forms of these types of incontinence as well as so-called overflow incontinence (e.g. in benign prostatic hyperplasia) or reflex incontinence (e.g. after spinal cord injury) occur. Further details can be found in Chutka, D. S. and Takahashi, P. Y., 1998, Drugs 560: 587-595.

Urinary urgency is the state of increased bladder muscle tension leading to voiding of urine (micturition) when the bladder is almost full (or when its capacity is exceeded). This muscle tension acts as a stimulus to pass urine. Increased urinary urgency is understood in this connection to mean in particular the occurrence of premature or more frequent and sometimes even painful urinary urgency up to so-called dysuria. This consequently leads to a significantly increased frequency of micturition. Causes may include, inter alia, inflammation of the bladder and neurogenic bladder disorders, as well as also bladder tuberculosis. However, all causes have not yet been elucidated.

Increased urinary urgency and also urinary incontinence are regarded as extremely unpleasant and there is therefore a clear need to achieve the greatest possible long-term improvement in patients affected by these medical conditions.

Increased urinary urgency and in particular urinary incontinence are normally treated with substances that act on the reflexes of the lower urinary tract (Wein A. J., 1998, Urology 51 (Suppl. 21): 43-47). In general these are medicaments that have a blocking effect on the detrusor muscle, which is responsible for the internal bladder pressure. These medicaments include for example parasympatholytics such as oxybutynin, propiverine or tolterodine, tricyclic antidepressants such as imipramine, or muscle relaxants such as flavoxate. Other medicaments that in particular increase the resistance of the urethra or cervix of the bladder have similarities with α-adrenoreceptors such as ephedrine, with β-adrenoreceptors such as clenbutarol, or are hormones such as oestradiol.

A detailed insight into the drugs and therapeutic methods that are used, especially as regards the anti-muscarinics and other peripherally acting substances, is given in the review article by K. E. Andersson et al. "The pharmacological treatment of urinary incontinence", BJU International (1999), 84, 923-947.

Certain diarylmethylpiperazines and diarylmethylpiperidines are also described in WO 93/15062 for this medical condition. Likewise Tramadol was shown to have a positive effect on bladder function in a rat model of rhythmic bladder contractions (Nippon-Shinyaku, WO 98/46216). Furthermore the relevant literature contains details of investigations on the characterisation of the opioid side effect of urinary retention, from which information has been obtained on the influencing of bladder functions by weak opioids such as diphenoxylate (Fowler et al., 1987 J. Urol. 138: 735-738) and meperidine (Doyle and Briscoe, 1976 Br. J. Urol. 48: 329-335), by mixed opioid agonists/antagonists such as buprenorphine (Malinovsky et al., 1998 Anesth. Analg. 87; 456-461; Drenger and Magora, 1989 Anesth. Analg. 69: 348-353), pentazocine (Shimizu et al. (2000) Br. J. Pharmacol. 131 (3): 610-616) and nalbuphine (Malinovsky et al., 1998, loc. cit.), as well as by powerful opioids such as morphine (Malinovsky et al., 1998, loc. cit.; Kontani and Kawabata, (1988); Jpn. J. Pharmacol. Sept.; 48(1): 31) and fentanyl (Malinovsky et al., 1998, loc. cit.). However, these investigations were generally carried out in analgesically effective concentrations.

It should be noted that treating the medical conditions of interest here involves the very long-term use of medicaments and, in contrast to many situations in which analgesics are used, patients suffer very unpleasant but not intolerable discomfort. Accordingly in this case—even more than with analgesics—care should be taken to avoid side effects if the patient does not wish to exchange one discomfort for another. Furthermore, in the long-term treatment of urinary incontinence analgesic effects are also largely undesirable.

SUMMARY OF THE INVENTION

It is an object of the present invention to provide substances or combinations of substances that are helpful in the treatment of increased urinary urgency or urinary incontinence.

Another object of the invention is to provide substances or combinations of substances that can be used to treat increased urinary urgency or urinary incontinence with fewer side effects and/or analgesic effects at the effective doses than medicaments known from the prior art.

A further object of the invention is to provide substances or combinations of substances that exhibit a synergistic effect in the treatment of urinary incontinence.

In one aspect, the present invention accordingly provides an active constituent salt of 1-dimethylamino-3-(3-methoxyphenyl)-2-methylpentan-3-ol formed from 1-dimethylamino-3-(3-methoxyphenyl)-2-methylpentan-3-ol and an active constituent selected from:

Ibuprofen,
(s)(+)Ibuprofen,
(S)(+)Naproxen,
Diclofenac,
acetylsalicylic acid,
Dipyron,
Indomethacin,
Ketoprofen,
Isoxicam,
Flurbiprofen,
Piroxicam or
phenylbutazone, with respect to 1-dimethylamino-3-(3-methoxyphenyl)-2-methylpentan-3-ol and/or the active constituent optionally in the form of the racemates, pure stereoisomers, in particular enantiomers or diastereomers, or in the form of mixtures of the stereoisomers, in particular the enantiomers or diastereomers, in an arbitrary mixture ratio.

In this connection it is particularly preferred if the active constituent salt is of (+)-(2R,3R)-1-dimethylamino-3-(3-methoxyphenyl)-2-methylpentan-3-ol.

The present invention also provides an active constituent salt of 3-(3-dimethylamino-1-ethyl-1-hydroxy-2-methylpropyl)-phenol formed from 3-(3-dimethylamino-1-ethyl-1-hydroxy-2-methylpropyl)-phenol and an active constituent selected from:
Ibuprofen,
(s)(+) Ibuprofen,
(S)(+)Naproxen,
Diclofenac,
acetylsalicylic acid,
Dipyron,
Indomethacin,
Ketoprofen,
Isoxicam,
Flurbiprofen,
Piroxicam or
phenylbutazone, with respect to 3-(3-dimethylamino-1-ethyl-1-hydroxy-2-methylpropyl)-phenol and/or the active constituent optionally in the form of the racemates, pure stereoisomers, in particular enantiomers or diastereomers, or in the form of mixtures of the stereoisomers, in particular the enantiomers or diastereomers, in an arbitrary mixture ratio.

In this connection it is particularly preferred if the active constituent salt is of (+)-(2R,3R)-3-(3-dimethyl-amino-1-ethyl-1-hydroxy-2-methylpropyl)-phenol.

The invention furthermore provides an ester of 3-(3-dimethylamino-1-ethyl-1-hydroxy-2-methylpropyl)-phenol according to formula I

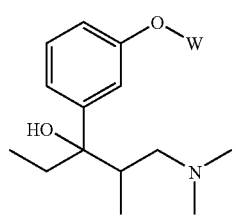

where W is selected from dehydroxylated:
Ibuprofen,
(s)(+)Ibuprofen,
(S)(+)Naproxen,
Indomethacin,
Diclofenac,
Dipyron,
Flurbiprofen,
Ketoprofen or
acetylsalicylic acid, optionally in the form of the racemates, pure stereoisomers, in particular enantiomers or diastereomers, or in the form of mixtures of the stereoisomers, in particular enantiomers or diastereomers, in an arbitrary mixture ratio; in the prepared form or in the form of their acids or their bases or in the form of their salts, in particular physiologically compatible salts, or in the form of their solvates, in particular hydrates.

In this connection it is particularly preferred if the ester according to formula I is present in the conformation of formula Ib

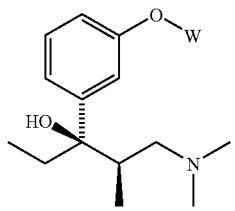

The invention also provides an ester according to formula II

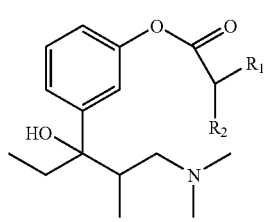

where $R_1$ is selected from aryl and heteroaryl, in each case substituted or unsubstituted, and $R_2$ is selected from H or $R_{1-3}$-alkyl or unsaturated, unsubstituted or singly or multiply substituted, optionally in the form of the racemates, pure stereoisomers, in particular enantiomers and diastereomers, or in the form of mixtures of the stereoisomers, in particular of the enantiomers or diastereomers, in an arbitrary mixture ratio; in the prepared form or in the form of their acids or their bases or in the form of their salts, in particular physiologically compatible salts, or in the form or their solvates, in particular the hydrates.

For esters according to the invention of the formula II it is particularly preferred if the ester is present in the conformation IIb

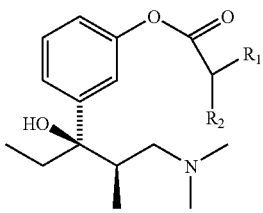

IIb

For esters according to the invention of formula II or IIb it is particularly preferred if $R_1$ is selected from

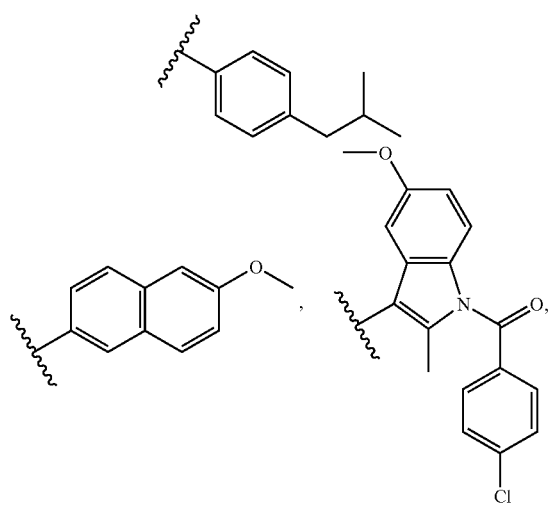

For esters according to the invention of formula II or IIb it is particularly preferred if $R_2$ is selected from H or $CH_3$.

The present invention also provides an ester according to the formula III

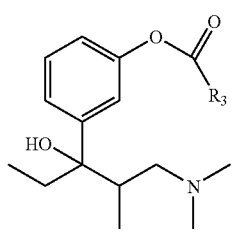

III where $R_3$ is selected from aryl and heteroaryl, in each case substituted or unsubstituted, optionally in the form of the racemates, pure stereoisomers, in particular enantiomers or diastereomers, or in the form of mixtures of the stereoisomers, in particular enantiomers or diastereomers, in an arbitrary mixture ratio; in the prepared form or in the form of their acids or their bases or in the form of their salts, in particular physiologically compatible salts, or in the form of their solvates, in particular hydrates.

For esters according to the invention of the formula III it is particularly preferred if the ester is present in the conformation IIIb

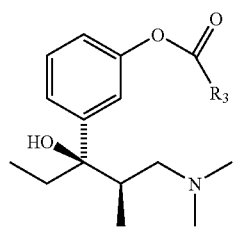

IIIb

For esters according to the invention of the formula III it is particularly preferred if $R_3$ is selected from

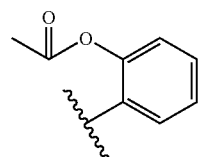

The present invention furthermore provides an ester according to formula IV

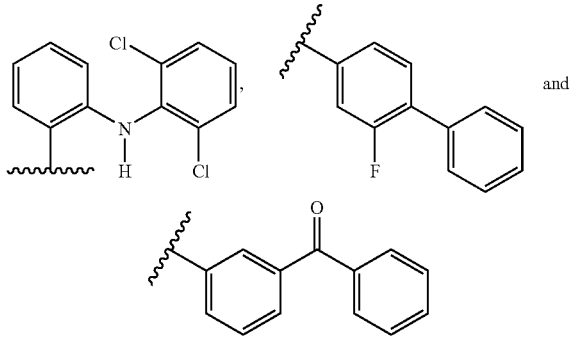

IV where $R_4$ is selected from aryl and heteroaryl, in each case substituted or unsubstituted, and $R_5$ is selected from H or $C_{1-3}$-alkyl, which is saturated or unsaturated, unsubstituted or singly or multiply substituted, optionally in the form of the racemates, pure stereoisomers, in particular enantiomers or diastereomers, or in the form of mixtures of the stereoisomers, in particular enantiomers and diastereomers, in an arbitrary mixture ratio; in the prepared form or in the form of their acids or their bases or in the form of their salts, in particular physiologically compatible salts, or in the form of their solvates, in particular hydrates.

For esters according to the invention of the formula IV it is particularly preferred if the ester is present in the conformation IVb

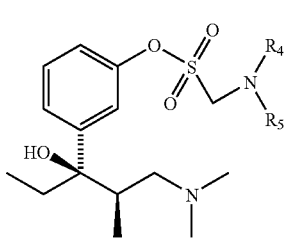

For esters according to the invention of the formula IV or IVb it is particularly preferred if $R_4$ is

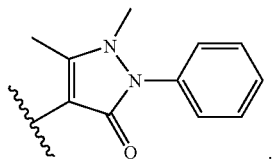

For esters according to the invention of the formula IV or IVb it is particularly preferred if $R_5$ is H or $CH_3$.

It has surprisingly been found that the aforementioned substances according to the invention have a significant positive effect on specific physiological parameters that are of importance in increased urinary urgency or urinary incontinence, i.e. affect either the threshold pressure, the intercontraction interval or reduce the rhythmic bladder contractions and/or bladder capacity. Each of these individual changes can significantly improve the symptoms experienced by affected patients.

Within the context of the present invention alkyl and cycloalkyl radicals are understood to denote saturated and unsaturated (but not aromatic) branched, unbranched and cyclic hydrocarbons, which may be unsubstituted or singly or multiply substituted. In this connection $C_{1-2}$-alkyl denotes C1- or C2-alkyl, $C_{1-3}$-alkyl denotes C1-, C2- or C3-alkyl, $C_{1-4}$-alkyl denotes C1-, C2-, C3- or C4-alkyl, $C_{1-5}$-alkyl denotes C1-, C2-, C3-, C4- or C5-alkyl, $C_{1-6}$-alkyl denotes C1-, C2-, C3-, C4-, C5- or C6-alkyl, $C_{1-7}$-alkyl denotes C1-, C2-, C3-, C4-, C5-, C6- or C7-alkyl, $C_{1-8}$-alkyl denotes C1-, C2-, C3-, C4-, C5-, C6-, C7- or C8-alkyl, $C_{1-10}$-alkyl denotes C1-, C2-, C3-, C4-, C5-, C6-, C7-, C8-, C9- or $C_{10}$-alkyl and $C_{1-18}$-alkyl denotes C1-, C2-, C3-, C4-, C5-, C6-, C7-, C8-, C9-, C10-, C11-, C12-, C13-, C14-, C15-, C16-, C17- or C18-alkyl. Furthermore $C_{3-4}$-cycloalkyl denotes C3- or C4-cycloalkyl, $C_{3-5}$-cycloalkyl denotes C3-, C4- or C5-cycloalkyl, $C_{3-6}$-cycloalkyl denotes C3-, C4-, C5- or C6-cycloalkyl, $C_{3-7}$-cycloalkyl denotes C3-, C4-, C5-, $C_6$- or C7-cycloalkyl, $C_{3-8}$-cycloalkyl denotes C3-, C4-, C5-, C6-, C7- or C8-cycloalkyl, $C_{4-5}$-cycloalkyl denotes C4- or C5-cycloalkyl, $C_{4-6}$-cycloalkyl denotes C4-, C5- or C6-cycloalkyl, $C_{4-7}$-cycloalkyl denotes C4-, C5-, C6- or C7-cycloalkyl, $C_{5-6}$-cycloalkyl denotes C5- or C6-cycloalkyl and $C_{5-7}$-cycloalkyl denotes C5-, C6- or C7-cycloalkyl. In relation to cycloalkyl, the term also includes saturated cycloalkyls in which 1 or 2 carbon atoms are replaced by a heteroatom, i.e. S, N or O. The term cycloalkyl however also includes in particular singly or multiply, preferably singly, unsaturated cycloalkyls without a heteroatom in the ring provided that the cycloalkyl does not form an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentyl-methyl, cyclohexyl, cycloheptyl, cyclooctyl, and also adamantyl, $CHF_2$, $CF_3$ or $CH_2OH$ as well as pyrazolinone, oxopyrazolinone, [1,4]dioxane or dioxolane.

In connection with alkyl and cycloalkyl it is understood—unless specifically defined otherwise—that the term substituted within the context of the present invention denotes the substitution of at least one (possibly also several) hydrogen atom(s) by F, Cl, Br, I, $NH_2$, SH or OH, wherein "multiply substituted" and "substituted" in the case of multiple substitution means that the substitution can occur multiply with the same or different substituents on different atoms as well as on the same atom, for example triply on the same C atom as in the case of $CF_3$, or at different positions as in the case of —CH(OH)—CH=CH—$CHCl_2$. Particularly preferred substituents here are F, Cl and OH. With regard to cycloalkyl, the hydrogen atom may also be replaced by $OC_{1-3}$-alkyl or $C_{1-3}$-alkyl (in each case singly or multiply substituted or unsubstituted), in particular by methyl, ethyl, n-propyl, i-propyl, $CF_3$, methoxy or ethoxy.

The term $(CH_2)_{3-6}$ is understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, the term $(CH_2)_{1-4}$ is understood to denote —$CH_2$—, —$CH_2$—$CH_2$—, —$CH_2$—$CH_2$—$CH_2$— and —$CH_2$—$CH_2$—$CH_2$—$CH_2$—, and the term $(CH_2)_{4-5}$ is understood to denote —$CH_2$—$CH_2$—$CH_2$—$CH_2$— and —$CH_2$—$CH_2$—$CH_2$—$CH_2$—$CH_2$—, etc.

The term aryl radical is understood to denote ring systems with at least one aromatic ring but without heteroatoms in also only one of the rings. Examples include phenyl, naphthyl, fluoranthenyl, fluorenyl, tetralinyl or indanyl, in particular 9H-fluorenyl or anthracenyl radicals, which may be unsubstituted or singly or multiply substituted.

The term heteroaryl radical is understood to mean heterocyclic ring systems with at least one unsaturated ring, which may contain one or more heteroatoms from the group comprising nitrogen, oxygen and/or sulfur, and may also be singly or multiply substituted. Examples from the group of heteroaryls include furan, benzofuran, thiophene, benzothiophene, pyrrole, pyridine, pyrimidine, pyrazine, quinoline, isoquinoline, phthalazine, benzo[1,2,5]-thiadiazole, benzothiazole, indole, benzotriazole, benzodioxolane, benzodioxane, carbazole and quinazoline.

In connection with aryl and heteroaryl, the term substituted denotes the substitution of the aryl or heteroaryl with $R^{22}$, $OR^{22}$, a halogen, preferably F and/or Cl, a $CF_3$, a CN, an $NO_2$, an $NR^{23}R^{24}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

In this connection the radical $R^{22}$ denotes H, a $C_{1-10}$-alkyl radical, preferably a $C_{1-6}$-alkyl radical, an aryl or heteroaryl radical, or an aryl or heteroaryl radical bonded via a $C_{1-3}$-alkylene group, wherein these aryl and heteroaryl radicals may not themselves be substituted by aryl or heteroaryl radicals, the radicals $R^{23}$ and $R^{24}$, which are identical or different, denote H, a $C_{1-10}$-alkyl radical, preferably a $C_{1-6}$-alkyl radical, an aryl radical, a heteroaryl radical, or an aryl or heteroaryl radical bonded via a $C_{1-3}$-alkylene group, wherein these aryl and heteroaryl radicals may not themselves be substituted by aryl or heteroaryl radicals, or the radical $R^{23}$ and $R^{24}$ together denote $CH_2CH_2OCH_2CH_2$, $CH_2CH_2NR^{25}CH_2CH_2$ or $(CH_2)_{3-6}$ and the radical $R^{25}$ denotes H, a $C_{1-10}$-alkyl radical, preferably a $C_{1-6}$-alkyl radical, an aryl or heteroaryl radical, or an aryl or heteroaryl radical bonded via a $C_{1-3}$-alkyl that is saturated or unsaturated, or via a $C_{1-3}$-alkylene group, wherein these aryl and heteroaryl radicals may not themselves be substituted by aryl or heteroaryl radicals.

The term salt denotes any form of the active constituent according to the invention in which this adopts an ionic form or is charged and is coupled to a counterion (a cation or anion), or is in solution. The term is also understood to include complexes of the active constituent with other molecules and ions, in particular complexes that are complexed via ionic interactions. In particular the term is understood to include (and this is also a preferred embodiment of the present invention) physiologically compatible salts, in particular physiologically compatible salts with cations or bases and physiologically compatible salts with anions or acids or also a salt formed with a physiologically compatible acid or a physiologically compatible cation.

The term physiologically compatible salt with anions or acids is understood within the context of the present invention to mean salts of at least one of the compounds according to the invention—generally protonated, for example on the nitrogen atom—as cation with at least one anion, that are physiologically compatible, especially when used in humans and/or mammals. Within the context of the present invention the term is particularly understood to mean the salt formed with a physiologically compatible acid, namely salts of the respective active constituent that are physiologically compatible, especially when used in humans and/or mammals. Examples of physiologically compatible salts of specific acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydrol$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride salt is particularly preferred.

The term salt formed with a physiologically compatible acid is understood within the meaning of the present invention to denote salts of the respective active constituent with inorganic or organic acids that are physiologically compatible, especially when used in humans and/or mammals. The hydrochloride is particularly preferred. Examples of physiologically compatible acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydrol$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid.

The term physiologically compatible salt with cations or bases is understood within the context of the present invention to mean salts of at least one of the compounds according to the invention—generally a (deprotonated) acid—as anion with at least one, preferably inorganic, cation, which are physiologically compatible, especially when used in humans and/or mammals. Particularly preferred are the salts of alkali and alkaline earth metals and also $NH_4^+$, but in particular (mono) or (di) sodium, (mono) or (di) potassium, magnesium or calcium salts.

The term salt formed with a physiologically compatible cation is understood within the context of the present invention to denote salts of at least one of the respective compounds as anion with at least one inorganic cation, which is physiologically compatible, especially when used in humans and/or mammals. Particularly preferred are salts of alkali and alkaline earth metals and also $NH_4^+$, but in particular (mono) or (di) sodium, (mono) or (di) potassium, magnesium or calcium salts. The hydrochloride is particularly preferred.

1-dimethylamino-3-(3-methoxyphenyl)-2-methylpentan-3-ol, (2RS,3RS)-1-dimethylamino-3-(3-methoxyphenyl)-2-methylpentan-3-ol, (+)-(2R,3R)-1-dimethylamino-3-(3-methoxyphenyl)-2-methylpentan-3-ol, (−)-(2S,3S)-1-dimethylamino-3-(3-methoxyphenyl)-2-methylpentan-3-ol, 3-(3-dimethylamino-1-ethyl-1-hydroxy-2-methylpropyl)-phenol, (2RS,3RS)-3-(3-dimethylamino-1-ethyl-1-hydroxy-2-methylpropyl)-phenol, (+)-(2R,3R)-3-(3-dimethylamino-1-ethyl-1-hydroxy-2-methylpropyl)-phenol, (−)-(2S,3S)-3-(3-dimethylamino-1-ethyl-1-hydroxy-2-methylpropyl)-phenol and their production are known from DE 44 26 245 A1 and U.S. Pat. No. 6,248,737 B1. The other active constituents with which these compounds are reacted are known analgesics that are commercially available and whose production is sufficiently well known to the person skilled in the art.

The esters and salts according to the invention are toxicologically harmless and medically effective.

The present invention accordingly also provides a medicament, preferably for treating increased urinary urgency or urinary incontinence, containing at least one active constituent salt according to the invention or an ester according to the invention, as well as optionally suitable additives and/or auxiliary substances. Suitable additives and/or auxiliary substances within the context of the present invention include all substances known to the person skilled in the art from the prior art for preparing galenical formulations. The choice of these auxiliary substances as well as the amounts thereof to be used depend on whether the medicament is to be administered orally, intravenously, intraperitoneally, intradermally, intramuscularly, intranasally, buccally or topically. For oral application preparations in the form of tablets, chewable tablets, sugar-coated pills, capsules, granules, drops, juices or syrups are suitable, while for parenteral, topical and inhalative application solutions, suspensions, readily reconstitutable dry preparations as well as sprays are suitable. A further possible form of application are suppositories for rectal use. The use in a depôt form, in dissolved form, in a carrier film or a plaster, optionally with the addition of agents promoting penetration of the skin, are examples of suitable percutaneous application forms. Examples of auxiliary substances and additives for oral application forms are disintegrants, lubricants, binders, fillers, mould release agents, optionally solvents, taste enhancers, sugars, in particular excipients, diluents, colourants, antioxidants, etc. For suppositories there may be used inter alia waxes or fatty acid esters, and for parenteral application agents there may be used excipients, preservatives, suspension auxiliaries, etc. The amounts of active ingredient to be administered to the patient vary depending on the patient's weight, on the type of application and the severity of the medical condition. The compounds according to the invention may be employed in delayed release form in preparations for oral, rectal or percutaneous use. Corresponding retard formulations, in particular in the form of a "once daily" preparation that has to be taken only once a day, are particularly preferred for use in the medical conditions covered by the invention.

Also preferred are medicaments that contain at least 0.05 to 90.0% of the active ingredient, in particular low effective dosages in order to avoid side effects or analgesic effects. Normally 0.1 to 5000 mg/kg, in particular 1 to 500 mg/kg and preferably 2 to 250 mg/kg body weight of at least one compound of the formula I are administered. However, the administration of 0.01 to 5 mg/kg, preferably 0.03 to 2 mg/kg and in particular 0.05 to 1 mg/kg body weight is also preferred and customary.

Auxiliary substances may for example include the following: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatins, sorbitol, inositol, mannitol, microcrystalline cellulose, methylcellulose, carboxymethylcellulose, cellulose acetate, shellac, cetyl alcohol, polyvinylpyrrolidone, paraffins, waxes, natural and synthetic gums, gum arabic, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soy bean oil, lecithin, sodium lactate, polyoxyethylene fatty acid esters and polyoxypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potassium carbonate, calcium phosphate, dicalcium phosphate, potassium bromide, potassium iodide, talcum, kaolin, pectin, crospovidone, agar and bentonite.

The medicaments and pharmaceutical compositions according to the invention are produced with the aid of agents, equipment, methods and processes well known in the prior art for pharmaceutical formulations, such as are described for example in "Remington's Pharmaceutical Sciences", Editor A. R. Gennaro, 17$^{th}$ Edition, Mack Publishing Company, Easton, Pa. (1985), in particular in Part 8, Chapters 76 to 93.

Thus for example, for a solid formulation such as a tablet the active ingredient may be granulated with a pharmaceutical carrier, for example conventional tablet constituents such as maize starch, lactose, sucrose, sorbitol, talcum, magnesium stearate, dicalcium phosphate or pharmaceutically acceptable gums, and pharmaceutical diluents, such as for example water, in order to form a solid composition that contains the active constituent in homgeneous distribution. A homogeneous distribution is understood here to mean that the active ingredient is uniformly distributed over the whole composition so that the latter can be subdivided without any difficulty into equally effective unit dose forms such as tablets, pills or capsules. The solid composition is then subdivided into unit dose forms. The tablets or pills of the medicament according to the invention or of the compositions according to the invention may also be coated or compounded in another way in order to prepare a dose form with a delayed-release action. Suitable coating agents include inter alia polymeric acids and mixtures of polymeric acids with materials such as for example shellac, cetyl alcohol and/or cellulose acetate.

Also, if the medicaments according to the invention exhibit only slight side effects it may for example be advantageous in order to avoid specific forms of dependence to use in addition to the compounds according to the invention also morphine antagonists, in particular naloxone, naltrexone and/or levallorphan.

The compounds may be used very effectively in the treatment of increased urinary urgency or urinary incontinence, especially in stress incontinence and urge incontinence. Accordingly the invention furthermore provides for the use of an active constituent salt according to the invention or an ester according to the invention for the production of a medicament for the treatment of increased urinary urgency or urinary incontinence.

The compounds are in addition highly effective analgesics, and accordingly the invention furthermore provides for the use of an active constituent salt according to the invention or an ester according to the invention for the production of a medicament for treating pain, in particular chronic, visceral, neuropathic or acute pain or inflammation pain.

In addition the invention also relates to a method for the treatment of increased urinary urgency, urinary incontinence or pain, in which compounds according to the invention are used.

The following examples serve to illustrate the invention without however restricting the subject matter of the invention thereto.

EXAMPLES

Example 1

List of Tested Substances

The following is a list of the compounds tested as regards their effectiveness:

| Name | Cmpd. No. |
|---|---|
| (2RS,3RS)-1-dimethylamino-3-(3-methoxyphenyl)-2-methylpentan-3-ol, hydrochloride | 1 |
| (+)-(2R,3R)-1-dimethylamino-3-(3-methoxyphenyl)-2-methylpentan-3-ol, hydrochloride | 2 |
| (−)-(2S,3S)-1-dimethylamino-3-(3-methoxyphenyl)-2-methylpentan-3-ol, hydrochloride | 21 |
| (2RS,3RS)-3-(3-dimethylamino-1-ethyl-1-hydroxy-2-methylpropyl)-phenol, hydrochloride | 7 |

Example 2

Cystometry Tests on Conscious Fresh Rats

Cystometry investigations were carried out on fresh female Sprague-Dawley rats according to the method of Ishizuka et. al. ((1997), Naunyn-Schmiedeberg's Arch. Pharmacol. 355: 787-793). Three days after implantation of bladder and venous catheters the animals were investigated in the conscious state while freely moving. The bladder catheter was connected to a pressure gauge and an injection pump. The animals were placed in metabolic cages that enable the volume of urine to be measured. Physiological saline solution was infused (10 ml/hour) into the emptied bladder and the bladder pressure and volume of urine were continuously recorded. After a stabilisation phase a 20-minute phase was recorded that was characterised by normal, reproducible micturition cycles. The following parameters among others were measured:

threshold pressure TP, bladder pressure immediately before micturition, bladder capacity BC, residual volume after prior micturition plus volume of infused solution during the filling phase, intercontraction interval ICI, i.e. the time interval between consecutive micturition.

An increase in the threshold pressure (TP) indicates an important therapeutic effect in one of the medical conditions covered by the invention. Also, the intercontraction interval (ICI) is an important parameter for measuring the physiological effectiveness of a substance in the treatment of urinary incontinence, as is the bladder capacity (BC). In this connection, on account of the widely differing causes of the symptoms of these disease patterns it is not necessary to influence positively all three parameters in order for a medicament to be effective. It is therefore completely sufficient if a positive effect is demonstrated in only one of these parameters in order for the medicament to be of use in urinary incontinence or increased urinary urgency.

After recording three reproducible micturition cycles to provide a baseline value, the test substances 1 (1.0 mg/kg), 2 (0.1; 0.3 and 0.5 mg/kg), 21 (0.5 mg/kg) and 7 (0.3 mg/kg) in a vehicle comprising 0.9% NaCl were applied intravenously and the effect on the cystometric parameters was recorded at 90 to 120 minutes. In the effect maximum the mean value of 3 micturition cycles was determined and recorded as a percentage change compared to the baseline value (Table 1).

TABLE 1

Influencing of the cystometric parameters by the test substances (change compared to the baseline value [%]); n corresponds to the number of experimental animals; significance (Student T-Test): * p < 0.005; * p < 1.01; *** p < 0.001

| Compound | TP Threshold Pressure | BC Bladder Capacity | ICI Inter-Contraction Interval |
|---|---|---|---|
| 1 | | | |
| 1.0 mg/kg iv (n = 9) | +94%** | +31%** | +42% |
| 2 | | | |
| 0.1 mg/kg iv (n = 5) | +28.5%** | +7.8%** | +15.6% |
| 0.3 mg/kg iv (n = 8) | +122%** | +33%** | +28%* |
| 0.5 mg/kg iv (n = 9) | +77.5%** | +20.6%** | +28.6%** |
| 21 | | | |
| 0.5 mg/kg iv (n = 8) | −1.1%** | +3%** | +10% |
| 7 | | | |
| 0.3 mg/kg iv (n = 7) | +95%** | +32%** | +2%* |

The investigated substances exhibit a positive effect on the bladder regulation and are therefore suitable for treating urinary incontinence.

It was found inter alia that, of the enantiomers of the racemic compound 1, the (+) enantiomer (compound 2) is very effective (and thus is a particularly preferred compound of the present invention), while the (−) enantiomer (compound 21) does not exhibit such a marked effect.

The following compounds (esters and salts) were synthesised:

In general, hereinafter (+)(2R,3R)-3-(3-dimethylamino-1-ethyl-1-hydroxy-2-methylpropyl)-phenol is identified as M1 and (+)(2R,3R)-1-dimethylamino-3-(3-methoxyphenyl)-2-methylpentan-3-ol is identified as M0.

Example 30

General Procedure for the Preparation of the Esters

Reaction Equation:

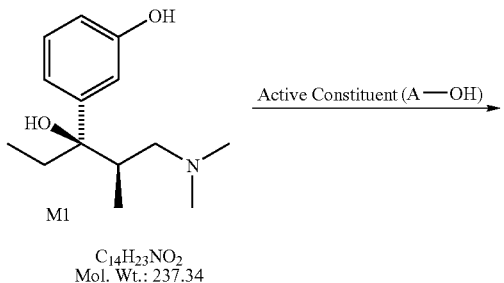

Batch quantities:

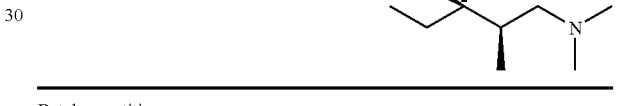

| X mmole | M1 | X' mg | 1.00 equiv. |
| Y mmole | A-OH | Y' mg | 0.95 equiv. |
| Z mmole | DCC (N,N,-dicyclohexylcarbodiimide) | Z' mg | 1.40 equivs. |
| V mmole | DMAP (N,N-dimethylaminopyridine) Dichloromethane | V' mg | 0.086 equiv. |

Apparatus:

three-necked flask (DHK), magnetic stirrer, nitrogen, ice bath

Procedure/Reaction conditions:

The apparatus is thoroughly heated (molecular sieve already in place). The acid and the M1 are weighed out and added, dissolved in dichloromethane. DMAP is added while stirring. The reaction mixture is cooled to 0° C. with an ice bath and the DCC dissolved in dichloromethane is added. The reaction mixture in the ice bath is slowly thawed out and stirred for 2 days.

The precipitate that is formed and the molecular sieve are filtered off (N,N-dicyclohexylurea) and post-washed with dichloromethane. The filtrate is concentrated to dryness at RT on a rotary evaporator. The residue is taken up in dichloromethane and refiltered.

Working-up:

The filtrate is washed with a 0.5 molar HCl solution. The phases are separated and the HCl phase is re-extracted by shaking with dichloronmethane. The organic phase is extracted by shaking with 10% sodium hydrogen carbonate solution, and the aqueous phase is rewashed with dichloromethane. The combined organic phases are dried over magnesium sulfate and concentrated by evaporation at

15

-continued

RT on a rotary evaporator. The product is dried for at least 1 hour.

Purification by column chromatography on silica gel

HCl Precipitation
Batch:

| Substance | 1.0 equiv. | |
|---|---|---|
| Trimethylchlorosilane | 1.2 equivs. | |
| | | ether |
| | | MEK (methyl ethyl ketone or 2-butanone) |

The base is dissolved in a small amount of MEK and ether is added until the solution becomes slightly turbid. Trimethylchlorosilane is added and the reaction mixture is stirred over 3 days at RT (room temperature). The hydrochloride preciptate is filtered off, washed with ether, and dried on a rotary evaporator.

Example 31

Ester with Flurbiprofen

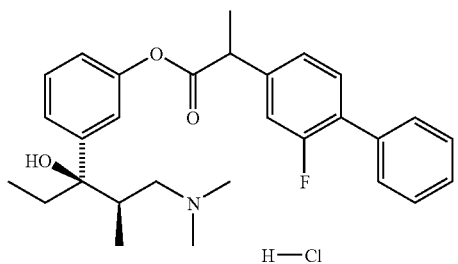

Reaction Equation:

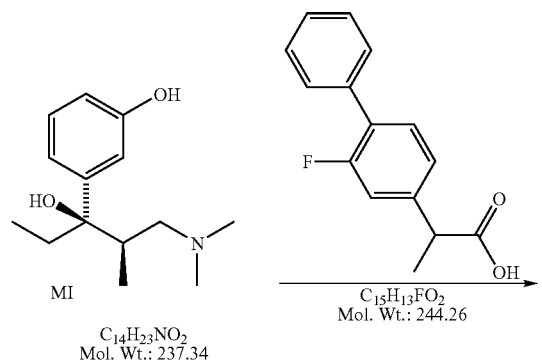

16

-continued

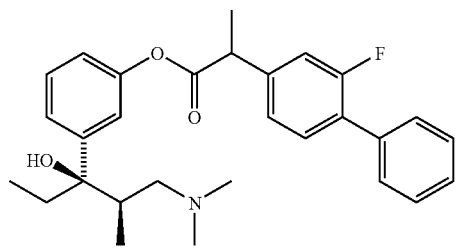

$C_{29}H_{34}FNO_3$
Mol. Wt.: 463.58

Batch quantities

| 2.11 mmole | M1 | 500 mg | |
|---|---|---|---|
| 2.00 mmole | Flurbiprofen | 488 mg | 0.95 equiv. |
| 2.95 mmole | DCC | 592 mg | 1.40 equiv. |
| 0.18 mmole | DMAP | 22 mg | 0.086 |
| | Dichloromethane | 25 ml | |

Apparatus:

100 ml DHK, nitrogen, magnetic stirrer, ice bath
Procedure/Reaction conditions:

The apparatus is thoroughly heated (molecular sieve already in place). The acid and the M1 are weighed out and added, dissolved in dichloromethane. DMAP is added while stirring. The reaction mixture is cooled to 0° C. with an ice bath and the DCC dissolved in dichloromethane is added. The reaction mixture in the ice bath is slowly thawed out and stirred for 2 days.
The precipitate that is formed and the molecular sieve are filtered off (N,N-dicyclohexylurea) and post-washed with 5 ml dichloromethane. The filtrate is concentrated to dryness at RT on a rotary evaporator. The residue is taken up in 5 ml dichloromethane and refiltered.
Working-up:

The filtrate is washed with a 0.5 molar HCl solution. The phases are spearated and the HCl phase is re-extracted by shaking with dichloromethane. The organic phase is extracted by shaking with 10% sodium hydrogen carbonate solution, and the aqueous phase is rewashed with dichloromethane. The combined organic phases are dried over magnesium sulfate and concentrated by evaporating at RT on a rotary evaporator. The product is dried for at least 1 hour.
Yield:

0.95 g 97% of theory

Purification by column chromatography

| Column: | Length: | 15 cm |
|---|---|---|
| | Diameter: | 6 cm |
| | Silica gel: | acidic |

Solvent: Ethyl acetate/methanol 5:1
Amount of substance to be separated: 0.95 g
Fraction step: 100 ml    Top product: 200 ml Fractions:

| Fr1 | Vl to 2 = | |
|---|---|---|
| Fr2 | 3 to 4 = | 360 mg |

TLC:

| Solvent: | EE/MeOH 5:1 |
|---|---|
| Detection: | UV/J$_2$ |
| Comparison substances: | substance-crude mixture |

HCl Precipitation:

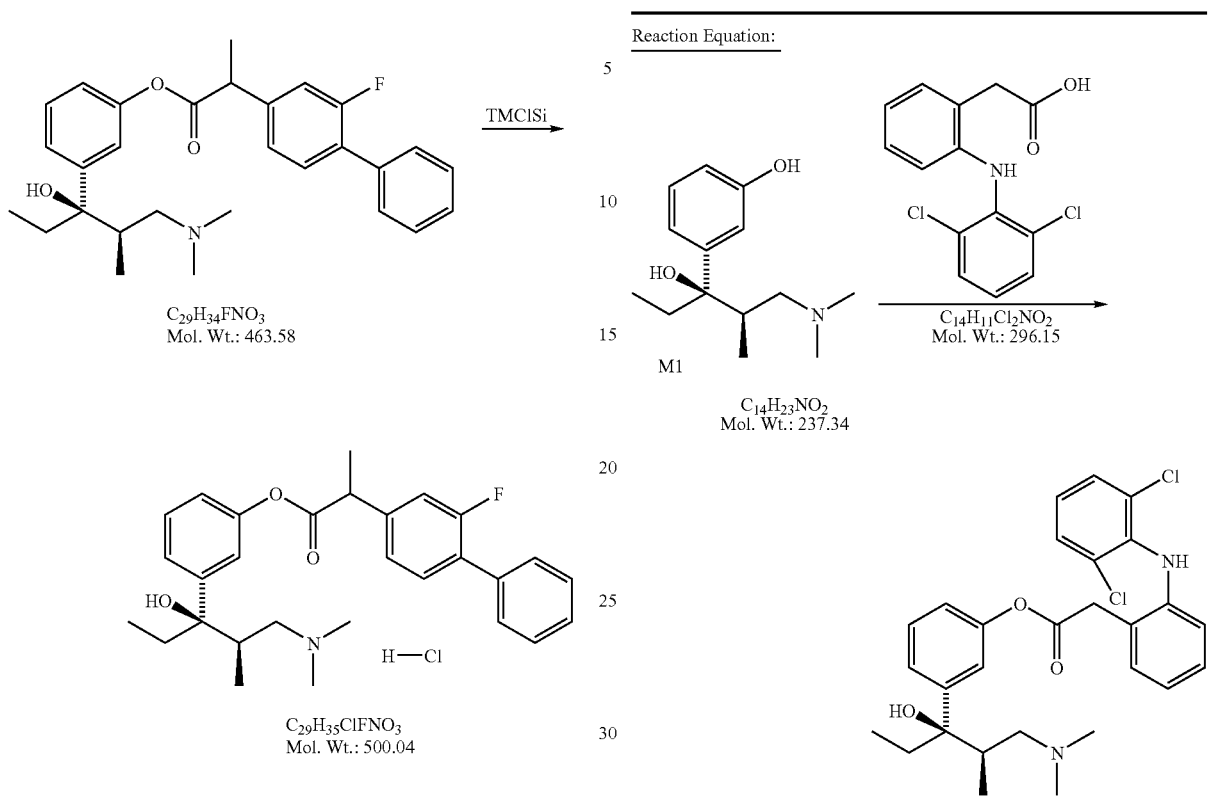

Dissolve the base in a small amount of MEK and add ether until the solution becomes slightly turbid. Add trimethylchlorosilane and stir at RT over 3 days. The colourless hydrochloride precipitate is filtered off, washed with ether and dried on a rotary evaporator.

Yield: 270 mg
Analysis: LC-MS
$^1$H NMR
M.P.: 128.3° C.

Example 32

Ester with Diclofenac

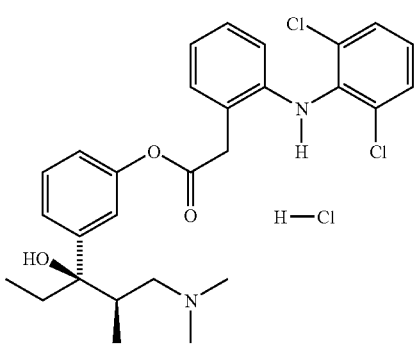

Batch quantities:

| | | | | |
|---|---|---|---|---|
| 4.21 mmole | M1 | 1000 mg | | |
| 4.00 mmole | Diclofenac | 1185 mg | 0.96 | equiv. |
| 5.89 mmole | DCC | 1180 mg | 1.40 | equivs. |
| 0.36 mmole | DMAP | 40 mg | 0.086 | equiv. |
| | Dichloromethane | 25 ml | | |

Apparatus:

100 ml DHK, magnetic stirrer, nitrogen
Procedure/Reaction conditions:

Place the molecular sieve in the apparatus and heat thoroughly. Flush with nitrogen. Dissolve M1 and acid in dichloromethane and add. While stirring, add DMAP and DCC dissolved in dichloromethane. Stir overnight.
TLC check with ethyl acetate/methanol 5:1 → new spot above M1
The precipitate that is formed and the molecular sieve are filtered off (N,N-dicyclohexylurea) and post-washed with 5 ml dichloromethane. The filtrate is concentrated by evaporation at RT on a rotary evaporator. The residue is taken up in 5 ml dichloromethane.
Working-up:

The filtrate is washed with a 0.5 molar HCl solution. Separate the phases and extract the HCl phase again by shaking with dichloromethane. Extract the organic phase by shaking with 10% sodium hydrogen carbonate solution and rewash the aqueous phase with dichloromethane. Dry the combined organic phases over magnesium sulfate and concentrate by evaporation at RT on a rotary evaporator.

-continued

Dry for 1 hour.
Yield:

2.48 g 114% of theory
Optical Properties:

Orange, clear, sticky like honey
Analyisis:

LC-MS
$^1$H-NMR
TLC check:

ethyl acetate/methanol 5:1 + ammonia

Purification by chromatography:

| Column: | Length: | 20 cm |
| --- | --- | --- |
|  | Diameter: | 6 cm |
|  | Silica gel: | acidic |

Solvent: Ethyl acetate/methanol 10:1 + 0.05% ammonia
Amount of substance to be separated: 2.48 g
Fraction step: 50 ml    Top product:

Fractions:

| Fr1 | V1 to 6 = |  |
| --- | --- | --- |
| Fr2 | 7 to 9 = | 930 mg |
| Fr3 | 10 to 15 = | 460 mg |
| Fr4 | NL = |  |

TLC:

| Solvent: | Ethyl acetate/methanol 10:1 + 0.05% ammonia |
| --- | --- |
| Detection: | UV/iodine |
| Comparison substances: | substance-crude mixture |

HCl Precipitation:

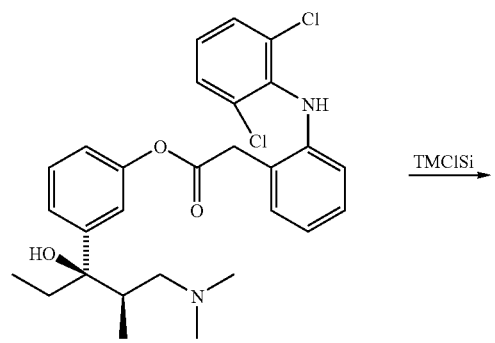

$C_{28}H_{32}Cl_2N_2O_3$
Mol. Wt.: 515.47

TMClSi →

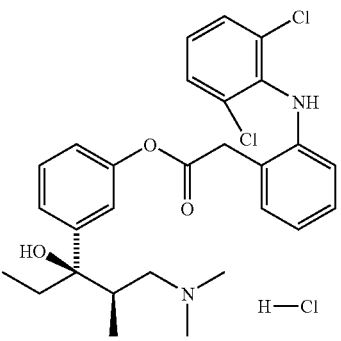

$C_{28}H_{33}Cl_3N_2O_3$
Mol. Wt.: 551.93

Batch 1:

| 1.8 mmole substance | 930 mg |  |
| --- | --- | --- |
| 2.2 mmole trimethylchlorosilane | 278 µl | 1.2 equivs. |
| Ether |  |  |
| Acetone |  |  |

Take up the base in ether and dissolve with a few drops of acetone. Add trimethylchlorosilane while cooling with ice. A colorless precipitate is immediately formed. Stir the mixture overnight.

| Yield: | 680 mg |  |
| --- | --- | --- |
| Analysis: | LC-MS | $^1$H NMR Fr2 |
|  |  | M.P.: 111.9° C. |

The following esters of Examples 33 to 39 were prepared as described hereinbefore (see Example 30):

Example 33

Ester with Ibuprofen

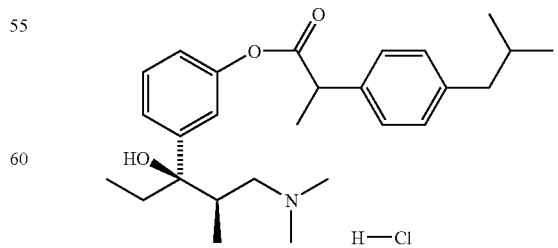

Example 34
Ester with (s)(+)-Ibuprofen
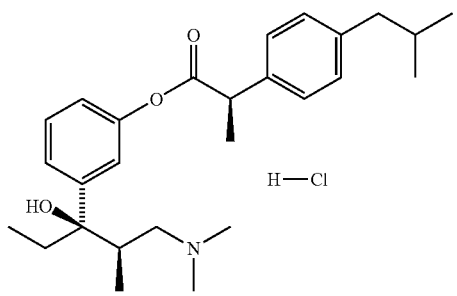
Example 35
Ester with (s)(+)-Naproxen
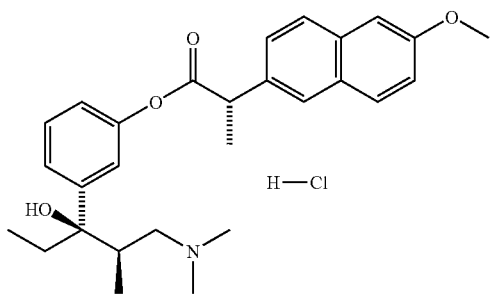
Example 36
Ester with Indomethacin
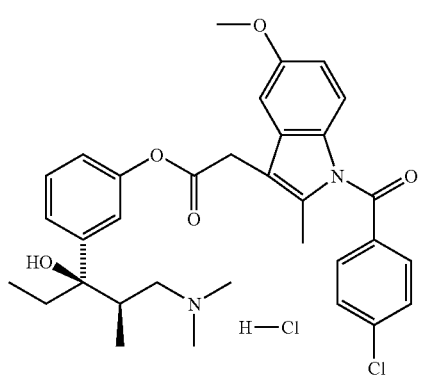
Example 37
Ester with Dipyron
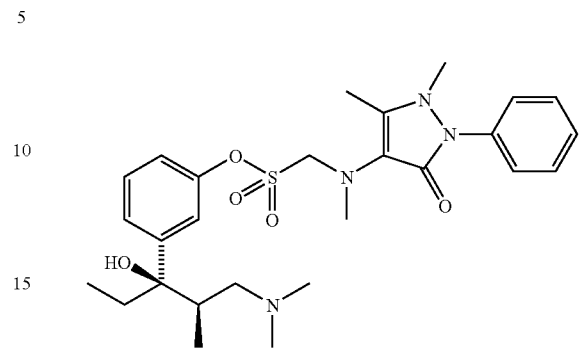
Example 38
Ester with Ketoprofen
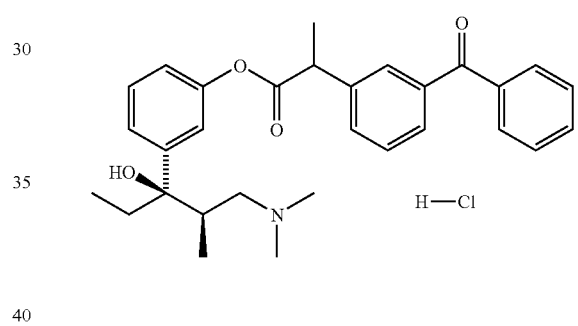
Example 39
Ester with Acetylsalicylic Acid
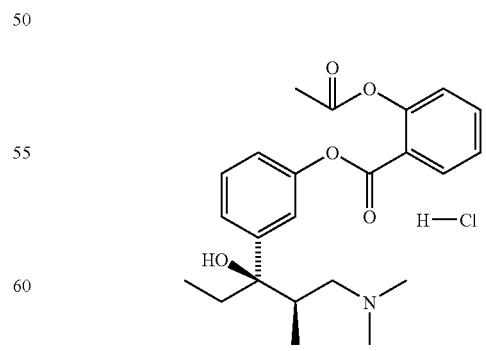

Example 40

General Procedure for the Preparation of the Salts of M1

Reaction Equation:

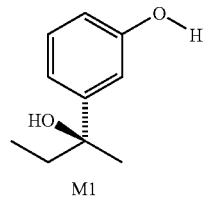

M1
$C_{14}H_{23}NO_2$
Mol. Wt.: 237.34

Active Constituent (H—S)
WIRKSTOFF (H—S)

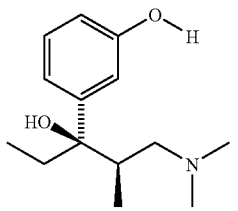

S—H
H—S $C_{14}H_{23}NO_2$
Mol. Wt.: 237.34

Batch quantities:

| | | |
|---|---|---|
| x mmole | M1 | z mg |
| x mmole | S | y mg |
| | Acetone | |

Apparatus:

50 ml EHK, reflux condenser, magnetic stirrer

Procedure/Reaction conditions:

Weigh out the base and acid and dissolve in as small an amount to acetone as possible. Stir the reaction mixture at RT to ca. 40° C. Optionally evaporate the solvent.

Example 41

Salt of M1 with (s)(+)Ibuprofen

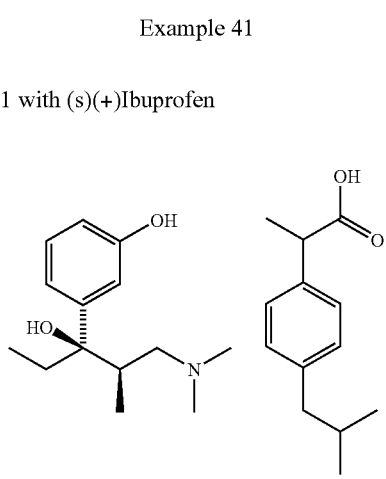

Reaction Equation:

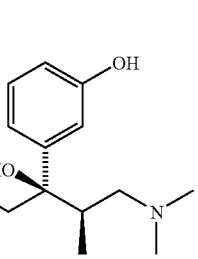 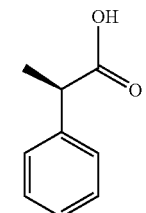

$C_{14}H_{23}NO_2$
Mol. Wt.: 237.34

$C_{13}H_{18}O_2$
Mol. Wt.: 206.28

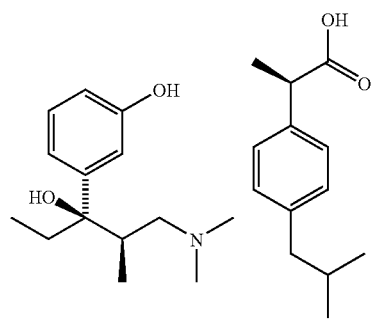

$C_{27}H_{41}NO_4$
Mol. Wt.: 443.62

Batch quantities:

| | | |
|---|---|---|
| 0.84 mmole | M1 | 200 mg |
| 0.84 mmole | (s) (+)Ibuprofen | 173 mg |
| | Acetone | |

Apparatus:

50 ml EHK, reflux condenser, magnetic stirrer

Procedure/Reaction conditions:

Weigh out the base and acid and dissolve in as small an amount of acetone as possible.
Stir overnight at RT.
No preciptate has formed. Heat the solution to 35-40° C. and stir for 4 hours at this temperature. After concentrating the product by evaporation (rotary evaporator), slowly cool to RT. A colourless precipitate now forms.

Yield:

360 mg 97% of theory

Analysis:

$^1$H NMR

Example 42

Salt of M1 with Flurbiprofen

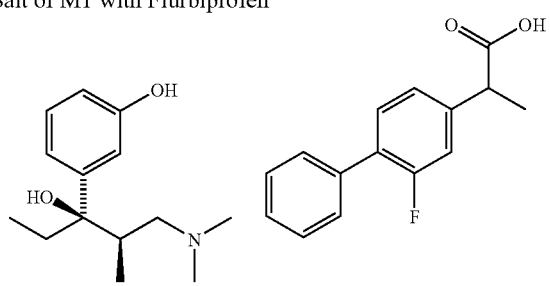

Reaction Equation:

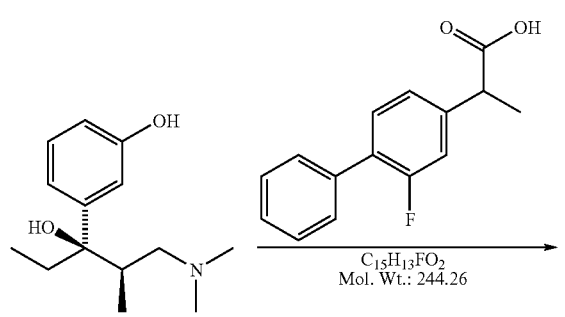

M1
$C_{14}H_{23}NO_2$
Mol. Wt.: 237.34

$C_{15}H_{13}FO_2$
Mol. Wt.: 244.26

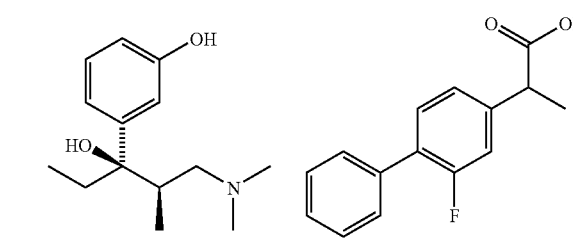

$C_{29}H_{36}FNO_4$
Mol. Wt.: 481.60

Batch quantities:

| | | |
|---|---|---|
| 0.88 mmole | M1 | 210 mg |
| 0.88 mmole | Flubiprofen | 215 mg |
| | Acetone | |

Apparatus:

50 ml EHK, magnetic stirrer, cooler
Procedure/Reaction conditions:

Weigh out the base and acid and dissolve in acetone. Stir the solution for 5 hours at 35-40° C. Continue to stir overnight at RT. After concentration by evaporation a light-coloured solid precipitates out.
Yield:

420 mg 99% of theory
Analysis:

$^1$H NMR M.P.: 64.9° C.

The following Examples 43 to 52 were prepared as described as hereinbefore (see Example 40):

Example 43

Salt of M1 with Ibuprofen

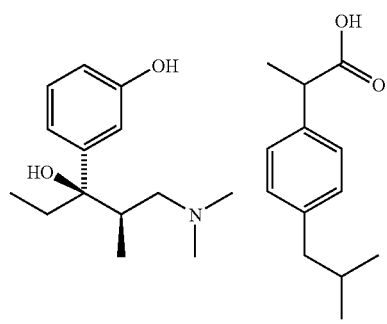

Example 44

Salt of M1 with (S)(+)Naproxen

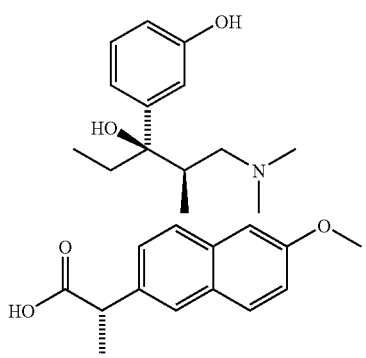

Example 45

Salt of M1 with Diclofenac

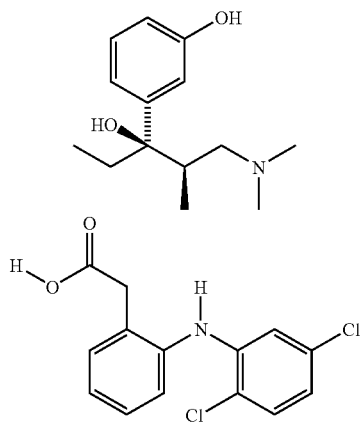

Example 46
Salt of M1 with Acetylsalicylic Acid
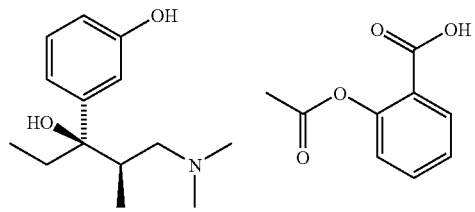
Example 47
Salt of M1 with Dipyron
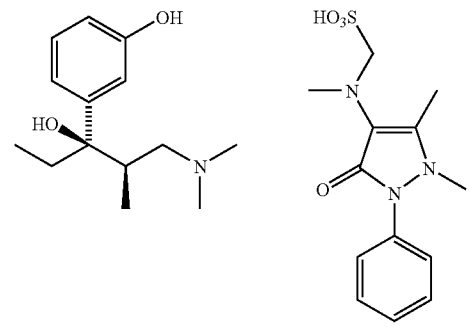
Example 48
Salt of M1 with Indomethacin
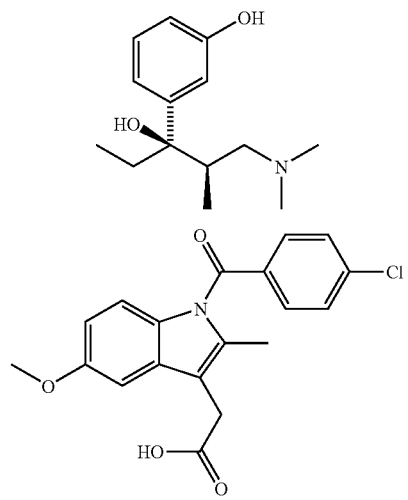
Example 49
Salt of M1 with Ketoprofen
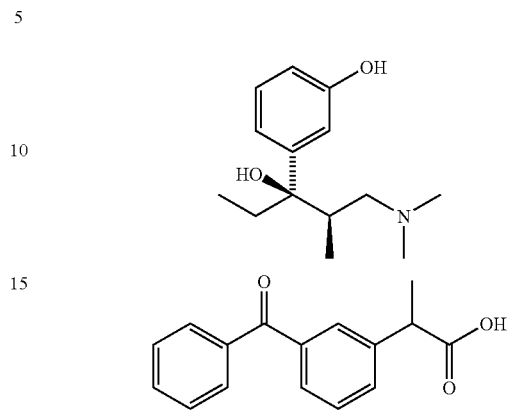
Example 50
Salt of M1 with Isoxicam
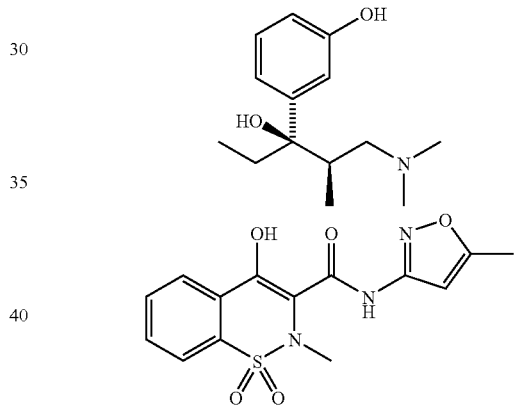
Example 51
Salt of M1 with Piroxicam
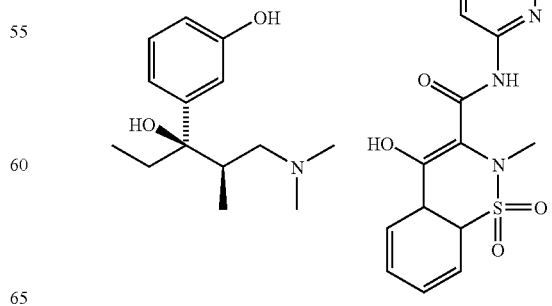

Example 52

Salt of M1 with Phenylbutazone

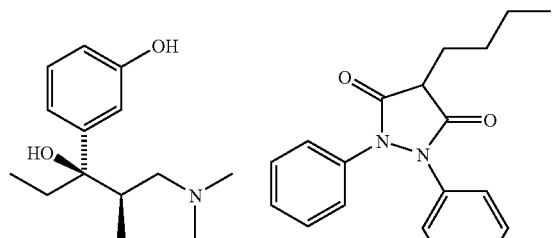

Example 60

General Process for the Preparation of the Salts of M0

Reaction Equation:

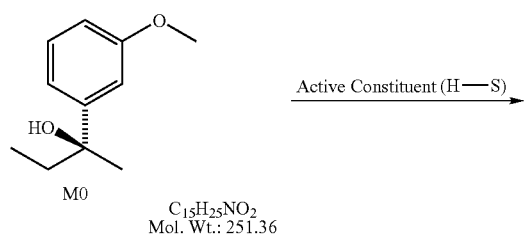

Batch quantities:

| | | |
|---|---|---|
| x mmole | M0 | z mg |
| x mmole | H—S | y mg |
| | Acetone | |

Apparatus:

50 ml EHK, reflux condenser, magnetic stirrer

Procedure/Reaction conditions:

Weigh out the base and acid and dissolve in as small an amount of acetone as possible. Stir at RT to ca. 40° C. Optionally evaporate the solvent.

Example 61

Salt of M0 and Diclofenac

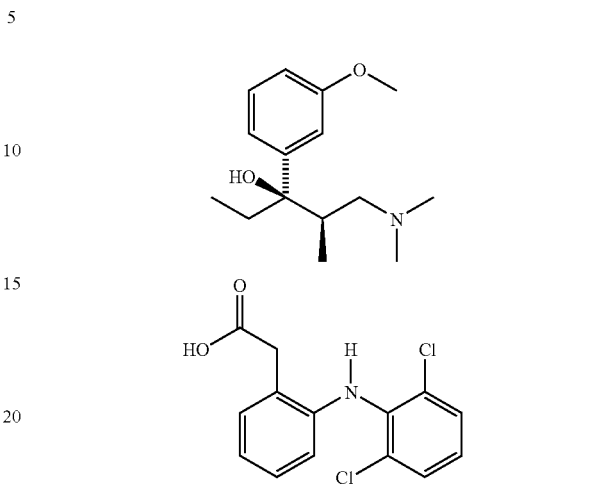

Reaction Equation:

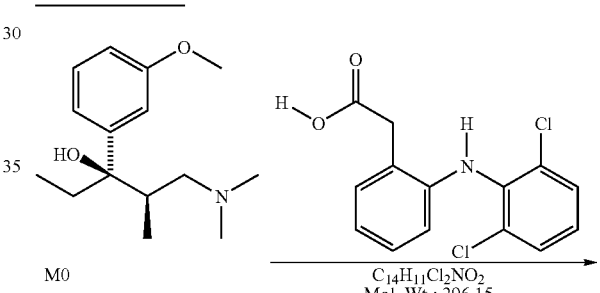

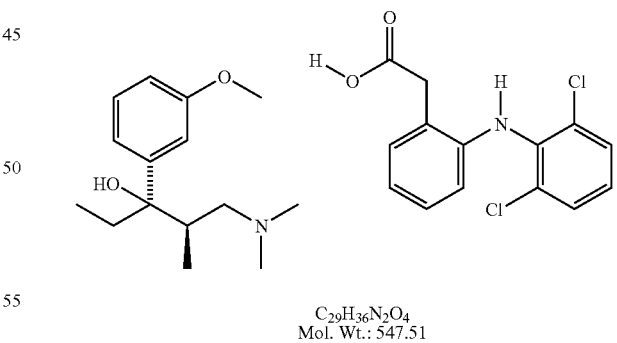

Batch quantities:

| | | |
|---|---|---|
| 1.18 mmole | M0 | 297 mg |
| 1.18 mmole | Diclofenac | 350 mg |
| | Acetone | |

-continued

Apparatus:

50 ml EHK, magnetic stirrer, cooler

Procedure/Reaction conditions:

Weigh out the base and acid and dissolve in acetone.

Stir at RT.

Working-up:

After concentration by evaporation, a white solid is obtained.

Yield:

640 mg 99% of theory

Analysis:

$^1$H NMR M.P.: 56.2° C.

Example 62

Salt of M0 with Indomethacin

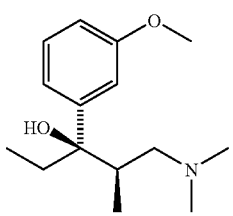

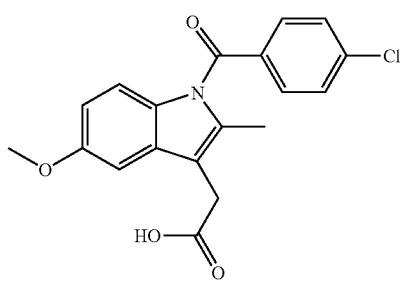

Reaction Equation:

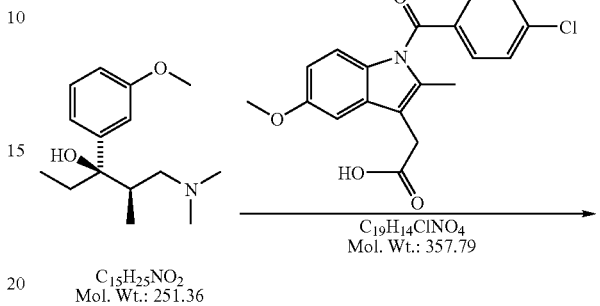

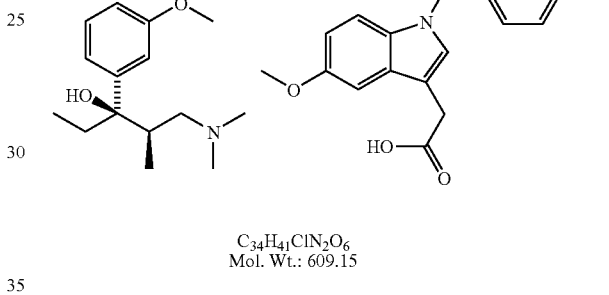

Batch quantites:

| 1.23 mmole | M0 | 297 mg |
|---|---|---|
| 1.23 mmole | Indomethacin | 350 mg |
| | Acetone | |

Apparatus:

50 ml EHK, magnetic stirrer, reflux condenser

Procedure/Reaction conditions:

Weigh out the base and acid and dissolve in as small an amount of acetone as possible. Stir for 5 hours at 35-40° C. Stir at RT.

Working-up:

After concentration by evaporation, a yellowish solid is obtained.

Yield:

740 mg 99% of theory

Analysis:

$^1$H NMR M.P.: 48.3° C.

The following salts of Examples 63 to 72 were prepared as described hereinbefore (see Example 60).

Example 63
Salt of M0 with Ibuprofen
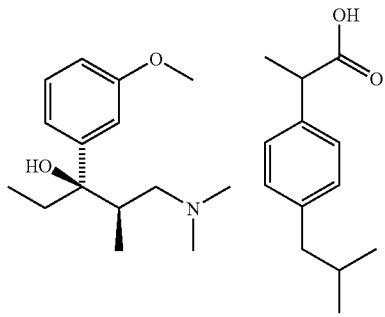
Example 64
Salt of M0 with (s)(+)Ibuprofen
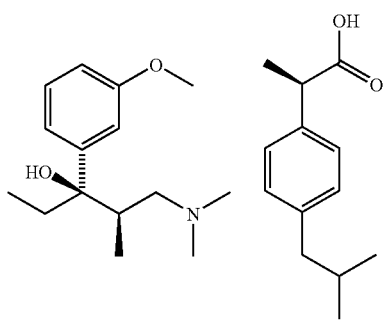
Example 65
Salt of M0 with (S)(+)Naproxen
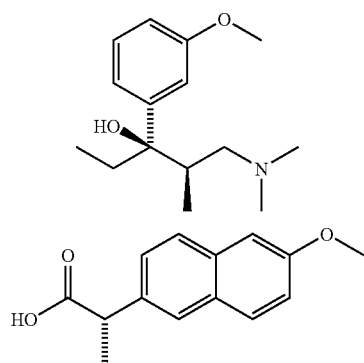
Example 66
Salt of M0 with Acetylsalicylic acid
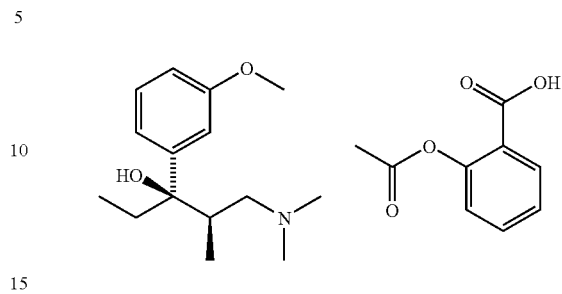
Example 67
Salt of M0 with Dipyron
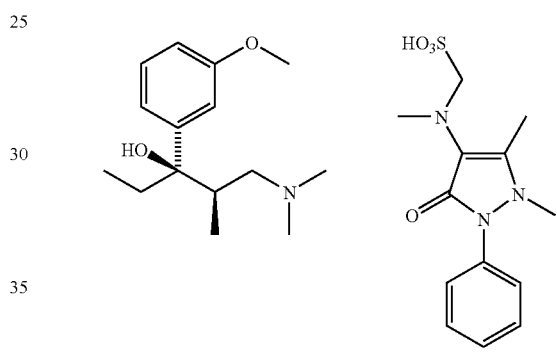
Example 68
Salt of M0 with Ketoprofen
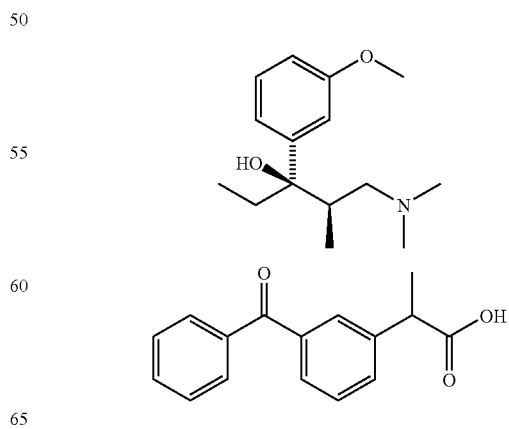

Example 69

Salt of M0 with Isoxicam

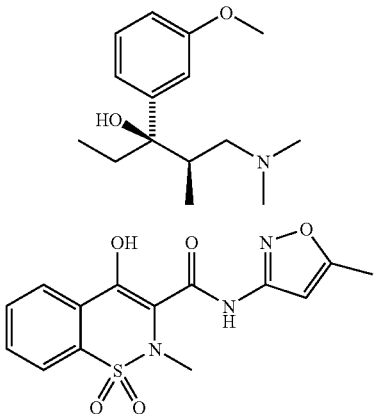

Example 70

Salt of M0 with Flurbiprofen

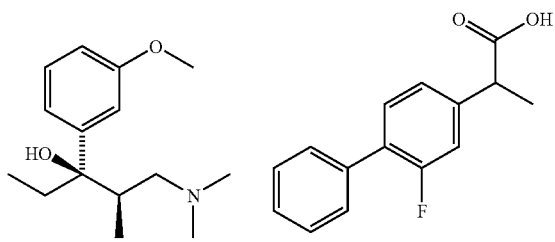

Example 71

Salt of M0 with Piroxicam

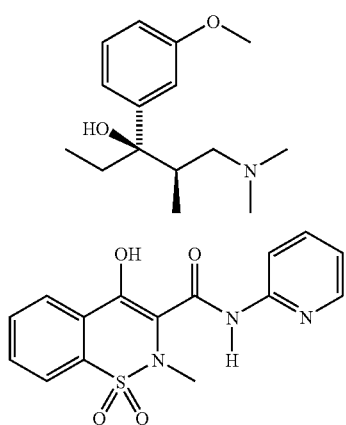

Example 72

Salt of M0 with Phenylbutazone

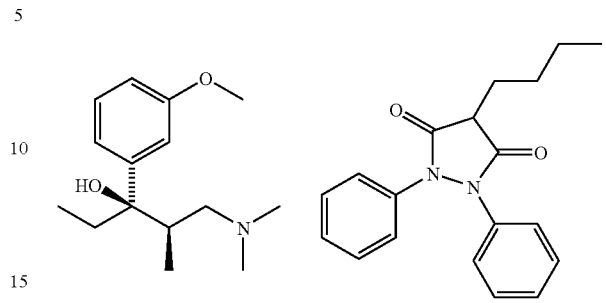

Example 100

Parenteral Application Form 20 g of active constituent salt of 1-dimethylamino-3-(3-methoxyphenyl)-2-methylpentan-3-ol with Diclofenac (Example 61) is dissolved at room temperature in 1 l of water for injection purposes and is then adjusted to isotonic conditions by addition of NaCl.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A pharmaceutical salt formed from a first constituent selected from the group consisting of 1-dimethylamino-3-(3-methoxyphenyl)-2-methylpentan-3-ol and 3-(3-dimethylamino-1-ethyl-1-hydroxy-2-methylpropyl)-phenol, and a second constituent selected from the group consisting of ibuprofen, (s)(+)ibuprofen, (S)(+)naproxen, diclofenac, acetylsalicylic acid, dipyron, indomethacin, ketoprofen, isoxicam, flurbiprofen, piroxicam and phenylbutazone.

2. A salt according to claim 1, wherein said first constituent is in the form of a pure enantiomer or a pure diastereoisomer.

3. A salt according to claim 1, wherein said first constituent is in the form of a racemic mixture or an arbitrary mixture of isomers.

4. A salt according to claim 1, wherein said second constituent is in the form of a pure enantiomer or a pure diastereoisomer.

5. A salt according to claim 1, wherein said second constituent is in the form of a racemic mixture or an arbitrary mixture of isomers.

6. A salt according to claim 1, wherein said first constituent is 1-dimethylamino-3-(3-methoxyphenyl)-2-methylpentan-3-ol.

7. A salt according to claim 1, wherein said first constituent is (+)-(2R,3R)-1-dimethylamino-3-(3-methoxy-phenyl)-2-methylpentan-3-ol.

8. A salt according to claim 1, wherein said first constituent is 3-(3-dimethylamino-1-ethyl-1-hydroxy-2-methylpropyl)-phenol.

9. A salt according to claim 1, wherein said first constituent is (+)-(2R,3R)-3-(3-dimethylamino-1-ethyl-1-hydroxy-2-methylpropyl)-phenol.

10. A pharmaceutical composition comprising a salt according to claim 1 and at least one pharmaceutical carrier, additive or auxiliary substance.

11. A method of treating or inhibiting increased urinary urgency or urinary incontinence in a patient in need thereof, said method comprising administering to said patient a pharmaceutically effective amount of a salt according to claim 1.

12. A method of treating or inhibiting pain in a patient in need thereof, said method comprising administering to said patient a pharmaceutically effective amount of a salt according to claim 1.

* * * * *